(12) United States Patent
Jeon et al.

(10) Patent No.: US 7,550,406 B2
(45) Date of Patent: *Jun. 23, 2009

(54) PHOSPHORUS-CONTAINING CATALYST COMPOSITION AND HYDROFORMYLATION PROCESS USING THE SAME

(75) Inventors: You Moon Jeon, Daejeon (KR); Dong Hyun Ko, Daejeon (KR); O Hak Kwon, Daejeon (KR); Sung Shik Eom, Daejeon (KR); Sang Gi Lee, Daejeon (KR); Ji Joong Moon, Daejeon (KR); Kwang Ho Park, Daejeon (KR)

(73) Assignee: LG Chem. Ltd. (KR)

( * ) Notice: Subject to any disclaimer, the term of this patent is extended or adjusted under 35 U.S.C. 154(b) by 68 days.

This patent is subject to a terminal disclaimer.

(21) Appl. No.: 10/576,219

(22) PCT Filed: Jul. 3, 2004

(86) PCT No.: PCT/KR2004/001647

§ 371 (c)(1),
(2), (4) Date: Apr. 14, 2006

(87) PCT Pub. No.: WO2005/120704

PCT Pub. Date: Dec. 22, 2005

(65) Prior Publication Data

US 2007/0093680 A1  Apr. 26, 2007

(30) Foreign Application Priority Data

Jun. 12, 2004  (KR) ............... 10-2004-0043335

(51) Int. Cl.
*B01J 31/22* (2006.01)
*C07F 9/06* (2006.01)

(52) U.S. Cl. .................................. 502/155; 548/412
(58) Field of Classification Search .......... 502/155; 548/412
See application file for complete search history.

(56) References Cited

U.S. PATENT DOCUMENTS

| 4,450,299 A | 5/1984 | Oswald et al. | ............ 568/454 |
|---|---|---|---|
| 4,668,651 A | 5/1987 | Billig et al. | ............ 502/158 |
| 4,694,109 A | 9/1987 | Devon et al. | ............ 568/454 |
| 5,233,093 A | 8/1993 | Pitchai et al. | ............ 568/454 |
| 5,491,266 A | 2/1996 | Babin et al. | ............ 568/449 |
| 5,710,344 A | 1/1998 | Breikss et al. | ............ 568/451 |
| 5,962,744 A | 10/1999 | Ojima et al. | ............ 568/454 |
| 6,855,657 B2* | 2/2005 | Zhang | ............ 502/166 |
| 2006/0058558 A1* | 3/2006 | Jeon et al. | ............ 568/454 |
| 2007/0123735 A1* | 5/2007 | Jeon et al. | ............ 568/455 |

OTHER PUBLICATIONS van der Slot et al. "Rhodium-Catalyzed Hydroformylation and Deuterioformylation with Pyrryol-Based Phosphorus Amidite Ligands: Influence of Electronic Ligand Properties" Organometallics, 2002, vol. 21, pp. 3873-3883.*

Paganelli et al. "Hydroformylation of functionalized olefins catalyzed by water-solubile rhodium carbonyl complexes" Journal of Molecular Catalysis A: Chemical, 2000, vol. 157, pp. 1-8.*

Billig et al "Oxo Process" Kirk-Othmer Encyclopedia of Chemical Technology, 1996, Wiley and Sons, pp. 1-17.*

Moloy, K.G., et al., "N-Pyrrolyl Phosphines: An Unexploited Class of Phosphine Ligands with Exceptional Acceptor Character," J. Am. Chem. Soc., vol. 117, pp. 7696-7710 (1995).

Bizarri, S.N., et al., "CEH Marketing Research Report: OXO Chemicals," SRI International, vol. 682.7000 A, pp. 1-121 (2002).

PCT International Search Report, Korean Intellectual Property Office, Date of Mailing: Mar. 11, 2005.

* cited by examiner

*Primary Examiner*—Rei-Tsang Shiao
*Assistant Examiner*—Joseph R Kosack
(74) *Attorney, Agent, or Firm*—Cantor Colburn LLP

(57) ABSTRACT

Provided are a catalyst composition comprising a bidentate ligand, a monodentate ligand, and a transition metal catalyst and a process of hydroformylation of olefins, comprising reacting the olefin compound with gas mixture of hydrogen and carbon monoxide with stirring at an elevated pressure and temperature in the presence of the catalyst composition to produce aldehyde. The present catalytic compositions show high catalytic activity, high normal-to-iso aldehyde selectivity, and high stability.

4 Claims, No Drawings

PHOSPHORUS-CONTAINING CATALYST COMPOSITION AND HYDROFORMYLATION PROCESS USING THE SAME

BACKGROUND OF THE INVENTION

1. Field of the Invention

The present invention relates to a phosphorous-containing catalyst composition and a hydroformylation process using the same, and more particularly, to a phosphorous-containing catalyst composition in which a combination of a monodentate phosphorous compound and a bidentate phosphorous compound is used as a ligand to a transition metal catalyst and a process of hydroformylation of olefin compounds comprising reacting the olefin compound with a gas mixture of hydrogen and carbon monoxide with stirring at elevated pressure and temperature in the presence of the above catalyst composition to produce aldehyde.

2. Description of the Related Art

The hydroformylation reaction, also known as the oxo reaction (found by Otto Roelen in 1938), includes reacting an olefin with a synthesis gas ($CO/H_2$) in the presence of a metal catalyst and a ligand to produce a linear (normal) aldehyde and branched (iso) aldehyde which has one more carbon atom than the olefin. In 2001, about 8,400,000 tons of various aldehydes (including its alcohol derivatives) were produced through the oxo reaction worldwide (*SRI Report*, November 2002, 682. 700A). The various aldehydes synthesized according to the oxo reaction are converted to acids and alcohols through oxidation and reduction reactions. The aldehydes may be subjected to an aldol condensation reaction, and then converted to acids and alcohols having a long alkyl chain through oxidation and reduction reactions. The obtained acids and alcohols are used as solvents, additives, raw materials for various plasticizers, and etc.

Catalysts which are used in the oxo reaction are mostly based on the cobalt (Co) or rhodium (Rh) metal. Depending on the types of ligands and the operating conditions, different N/I (ratio of linear (normal) isomer to branched (iso) isomer) selectivity of aldehyde is obtained.

In addition to cobalt (Co) and rhodium (Rh), iridium (Ir), ruthenium (Ru), osmium (Os), planitum (Pt), palladium (Pd), iron (Fe), and nickel (Ni) can be used as a central metal in the catalyst for the oxo reaction. Catalytic activities of these metal complexes can be ordered as follows: Rh>>Co>Ir, Ru>Os>Pt>Pd>Fe>Ni. Therefore, most research and development have been focused on rhodium and cobalt. Examples of ligands in the catalyst may include phosphine ($PR_3$, $R=C_6H_5$, $n-C_4H_9$), phosphine oxide ($O=P(C_6H_5)_3$), phosphite, amine, amide, and isonitrile. There exist rarely ligands that are more advantageous in view of catalytic activity, stability and cost than triphenylphosphine (TPP). Thus, in most oxo reactions, Rh metal is used as a catalyst and TPP is used as a ligand. In addition, to increase the stability of a catalytic system, TPP ligand is used in an amount of at least 100 equivalent of the catalyst.

Eastman Kodak Company and Union Carbide Company (merged into Dow) developed a bidentate phosphine ligand having high catalytic activity and high N/I selectivity, respectively (see, U.S. Pat. Nos. 4,694,109 and 4,668,651).

Moloy and coworkers developed N-pyrrolyl phosphine which shows high activity and selectivity (*JACS* 1995, 117, 7696).

U.S. Pat. No. 5,710,344 describes a process for the preparation of linear aldehydes by hydroformylation using a bidentate ligand which contains at least one P—C or P—N bond.

SUMMARY OF THE INVENTION

The present invention provides a hydroformylation catalyst composition comprising a bidentate ligand, a monodentate ligand and a transition metal catalyst which have higher catalytic activity, while maintaining the same selectivity to normal aldehyde or iso aldehyde (N/I selectivity) as in the case of using a bidentate ligand alone and stabilize the catalytic system.

The present invention also provides a process of hydroformylation of olefin compounds, comprising reacting the olefin compound with a gas mixture of hydrogen and carbon monoxide with stirring at an elevated pressure and temperature in the presence of the above catalyst composition to produce aldehyde.

According to an aspect of the present invention, there is provided catalyst composition comprising a bidentate ligand represented by formula 1, a monodentate ligand represented by formula 2, and a transition metal catalyst represented by formula 3:

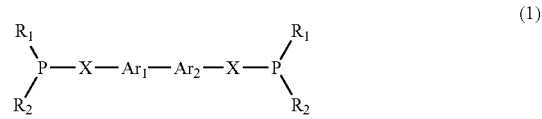

(1)

wherein
each of $R_1$ and $R_2$ is a substituted or unsubstituted C1-20 alkyl group; a substituted or unsubstituted C1-20 alkoxy group; a substituted or unsubstituted C5-20 cycloalkane or cycloalkene; a substituted or unsubstituted C6-36 aryl group; a substituted or unsubstituted C1-20 heteroalkyl group; a substituted or unsubstituted C4-36 heteroaryl group; or a substituted or unsubstituted C4-36 heterocyclic group,
$Ar_1$-$Ar_2$ is a bisaryl compound, and
X is oxygen (O) or sulfur (S),

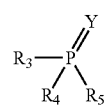

(2)

wherein
each of $R_3$, $R_4$ and $R_5$ is a substituted or unsubstituted C1-20 alkyl group; a substituted or unsubstituted C1-20 alkoxy group; a substituted or unsubstituted C5-20 cycloalkane or cycloalkene; a substituted or unsubstituted C6-36 aryl group; a substituted or unsubstituted C1-20 heteroalkyl group; a substituted or unsubstituted C4-36 heteroaryl group; or a substituted or unsubstituted C4-36 heterocyclic group, each of $R_3$, $R_4$ and $R_5$ being optionally substituted with nitro (—$NO_2$), fluorine (F), chlorine (Cl), bromine (Br), or a C1-4 alkyl group, and
Y is oxygen (O) or sulfur (S),

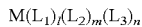 (3)

wherein
M is a transition metal,
each of $L_1$, $L_2$ and $L_3$ is hydrogen, CO, acetylacetonato, cyclooctadiene, norbornene, chlorine, or triphenylphosphine, and
each of l, m and n is a number of 0 to 5, provided that all l, m and n are not zero simultaneously.

According to another aspect of the present invention, there is provided a process of hydroformylation of olefins, comprising reacting the olefin compound with gas mixture of hydrogen and carbon monoxide with stirring at elevated pressure and temperature in the presence of the above catalyst composition to produce aldehyde.

The olefin compound may be represented by formula 4:

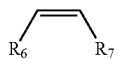

(4)

wherein each of $R_6$ and $R_7$ is hydrogen, a C1-20 alkyl group, fluorine (—F), chlorine (—Cl), bromine (—Br), trifluoromethyl (—CF$_3$), or a C6-20 phenyl group substituted with 0 to 5 substituents selected from the group consisting of nitro (—NO$_2$), fluorine (—F), chlorine (—Cl), bromine (—Br), methyl, ethyl, propyl and butyl.

DETAILED DESCRIPTION OF THE INVENTION

The catalyst composition according to an embodiment of the present invention comprises a bidentate ligand, a monodentate ligand and a transition metal catalyst.

The bidentate ligand represented by formula 1 may be one in which each of $R_1$ and $R_2$ is pyrrole, phenyl, or indole, and the phosphorous is directly linked to a nitrogen atom.

In formula 1, the bisaryl compound $Ar_1$-$Ar_2$ may be represented by either formula 5 or formula 6:

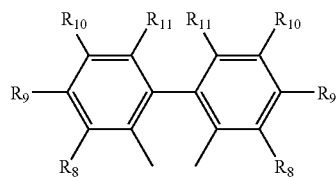

(5)

wherein each of $R_8$, $R_9$, $R_{10}$, and $R_{11}$ is hydrogen, a C1-20 alkyl group, a C6-20 aryl group, a triarylsilyl group, a trialkylsilyl group, a carboalkoxy group, a carboaryloxy group, an aryloxy group, an alkoxy group, an alkylcarbonyl group, an arylcarbonyl group, an amide group, a halogen atom, or a nitrile group, the carboalkoxy group being represented by —CO$_2$R (wherein R is a C1-20 alkyl group or a C6-20 aryl group), and preferably, $R_8$ may be methyl, methoxy, or t-butyl group, $R_9$ may be hydrogen, $R_{10}$ may be methyl, methoxy, or t-butyl, and $R_{11}$ may be methyl or hydrogen,

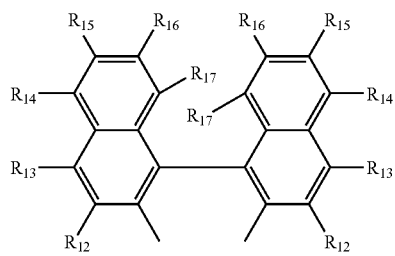

(6)

wherein each of $R_{12}$, $R_{13}$, $R_{14}$, $R_{15}$, $R_{16}$, and $R_{17}$ is hydrogen, a C1-20 alkyl group, a C6-20 aryl group, a triarylsilyl group, a trialkylsilyl group, a carboalkoxy group, a carboaryloxy group, an aryloxy group, an alkoxy group, an alkylcarbonyl group, an arylcarbonyl group, an amide group, a halogen atom, a nitrile group, the carboalkoxy group being represented by —CO$_2$R (wherein R is a C1-20 alkyl group or a C6-20 aryl group).

The monoidentate ligand represented by formula 2 may be one in which Y is oxygen (O), each of $R_3$, $R_4$, and $R_5$ is phenyl, phenyloxy, cyclohexyl, or t-butyl.

In the transition metal catalyst, the transition metal M may be cobalt (Co), rhodium (Rh), or iridium (Ir). Specific examples of the transition metal catalyst may include acetylacetonatodicarbonylrhodium (Rh(AcAc)(CO)$_2$), acetylacetonatocarbonyltriphenylphosphinerhodium (Rh(AcAc)(CO)(TPP)), hydridocarbonyltri(triphenylphosphine)rhodium (HRh(CO)(TPP)$_3$), acetylacetonatodicarbonyliridium (Ir(AcAc)(CO)$_2$), or hydridocarbonyltri(triphenylphosphine)iridium (HIr(CO)(TPP)$_3$).

In the catalyst composition, the concentration of the transition metal may be 50 to 500 ppm based on the amount of the catalyst composition. If the concentration of the transition metal is less than 50 ppm, the hydroformylation reaction rate can be reduced, which is commercially undesirable. If the concentration of the transition metal is more than 500 ppm, it is not cost competitive, since the transition metal is very expensive. In addition, the reaction rate is not advantageously increased, even at the concentration of more than 500 ppm.

According to the embodiment of the present invention, if a monodentate ligand is added to a catalyst composition comprising a Rh metal and a bidentate ligand, the catalytic activity can be increased in the hydroformylation reaction, with high N/I selectivity due to the bidentate ligand maintained. Moreover, even when an excess of the monodentate ligand is added, the catalytic activity and N/I selectivity are not reduced and the catalytic system can be stabilized. It appears that these advantages are derived since the monodentate ligand has a weak coordination to the metal center of the catalyst and does not interfere with the interaction between the transition metal and the bidentate ligand.

To obtain these advantages, the concentration of the bidentate ligand is 0.5 to 20 mol and the concentration of the monodentate ligand is 0.1 to 200 mol, respectively per mol of the transition metal. Preferably, the molar ratio of the bidentate ligand to Rh metal is 1 to 10 and the molar ratio of the monodentate ligand to Rh metal is 0.5 to 100, respectively per mol of the transition metal. If the molar ratio of the bidentate ligand to Rh metal is less than 0.5, the catalytic stability could be reduced. If the molar ratio of the bidentate ligand to Rh metal is more than 20, the catalytic activity could be reduced significantly. If the significantly of the monodentate ligand to Rh metal is less than 0.1, the catalytic activity could not be increased. If the significantly of the monodentate ligand to Rh metal is more than 200, it is not economical.

Advantageously, the transition metal catalyst may be acetylacetonatodicarbonylrhodium (Rh(AcAc)(CO)$_2$), the bidentate ligand may be 1,1'-biphenyl-2,2'-diyl-bis(dipyrrolylphosphoramidite) (BPO—P(Pyl)$_2$), and the monodentate ligand may be triphenylphosphine oxide (TPPO).

The olefin compound may be a compound selected from the group consisting of ethene, propene, 1-butene, 1-pentene, 1-hexene, 1-octene, and styrene.

The solvent used in the hydroformylation reaction according to the embodiment of the present invention may include aldehydes, such as propane aldehyde, butyraldehyde, and valeraldehyde; ketones, such as acetone, methyl ethyl ketone, methyl isobutyl ketone, acetophenone, and cyclohexanone; aromatics, such as benzene, toluene, and xylene; halogenated aromatics including ortho-dichlorobenzene; ethers, such as tetrahydrofuran, dimethoxy ethane, and dioxane; haloge nated paraffins including methylene chloride; paraffinic hydrocarbons such as heptane, preferably various aldehydes and aromatics, such as toluene.

The composition of the synthesis gas $CO/H_2$ used in the hydroformylation reaction according to the embodiment of the present invention can vary within a wide range. The molar ratio of $CO/H_2$ may be about 5:95 to 70:30, preferably about 40:60 to 60:40, and best is about 1:1.

The temperature of the hydroformylation reaction may be generally about 20 to 180° C., preferably about 50 to 150° C. The pressure of the hydroformylation reaction may be generally about 1 to 700 bar, preferably 1 to 300 bar.

Hereinafter, the present invention will be in more detail explained with reference to the following examples and not intended to limit the scope of the present invention.

Examples 1 to 12

Hydroformylation of Propene Using Acetylacetonatodicarbonylrhodium (Rh(AcAc)(CO)$_2$) Catalyst, a Bidentate Phosphorous compound and a Monodentate Phosphorous Compound 10.0 mg (37.8 mmol) of Rh(AcAc)(CO)$_2$ catalyst, 0.2 mL of hexadecane, which is an internal standard of GC analysis, a bidentate ligand BPO—P(Pyl)$_2$ and a monodentate ligand TPPO were added in toluene so that a total amount of the solution is 100 mL, each ratio of the bidentate ligand and the monodentate ligand to rhodium being listed in Table 1, and charged into a reactor (High Throughput Screening Unit (HTS), manufactured by Auto Clave). A gas mixture of propene:CO:H$_2$ in a molar ratio of 1:1:1 was injected into the reactor to maintain a pressure at 6 bar in the reactor. Then, the mixture was reacted while stirring at 85° C. for 2.5 hours.

The applied catalyst and ligands, the molar ratio of each ligand to the catalyst, the reaction temperature, the N/I selectivity, and the catalytic activity were listed in Table 1.

In Table 1, the N/I value represent the relative ratio of normal-butyraldehyde and iso-butyraldehyde produced. Each yield of the aldehyde was obtained by GC analysis based on the amount of the hexadecane added as an internal standard.

To calculate the catalytic activity of the each reaction, the total amount of the produced normal butyraldehyde and iso butyraldehyde was divided by the molecular weight of butyraldehyde, by the concentration of the catalyst, and by the reaction time. The catalytic activity is expressed in mol$_{(BAL)}$/mol$_{(Rh)}$/h.

Comparative Example 1

Hydroformylation of Propene Using Acetylacetonatodicarbonylrhodium (Rh(AcAc)(CO)$_2$) Catalyst and Triphenylphosphine (TPP)

The experiment for catalytic activity was performed in the same manner as in Example 1 except that TPP was used alone as a ligand and a molar ratio of ligand to rhodium was 100. The result is shown in Table 2.

Comparative Example 2

Hydroformylation of Propene Using Acetylacetonatodicarbonylrhodium (Rh(AcAc)(CO)$_2$) Catalyst and Tripyrrolylphosphine (P(Pyl)$_3$)

The experiment for catalytic activity was performed in the same manner as in Comparative Example 1 except that P(Pyl)$_3$ was used instead of TPP as a ligand and a molar ratio of ligand to rhodium was 50. The result is shown in Table 2.

Comparative Examples 3 to 5

Hydroformylation of Propene Using Acetylacetonatodicarbonylrhodium (Rh(AcAc)(CO)$_2$) Catalyst and 1,1'-biphenyl-2,2'-diyl-bis(dipyrrolylphosphoramidite) (BPO—P(Pyl)$_2$)

The experiments for catalytic activity were performed in the same manner as in Comparative Example 1 except that BPO—P(Pyl)$_2$ was used instead of TPP as a ligand and molar ratios of ligand to rhodium were 1, 3 and 5, respectively. The results are shown in Table 2.

Comparative Example 6

Hydroformylation of Propene Using Acetylacetonatocarbonyltriphenylphosphinerhodium (Rh(AcAc)(CO)(TPP)) Catalyst and 1,1'-biphenyl-2,2'-diyl-bis(dipyrrolylphosphoramidite) (BPO—P(Pyl)$_2$)

The experiment for catalytic activity was performed in the same manner as in Comparative Example 4 except that Rh(AcAc)(CO)(TPP) was used instead of Rh(AcAc)(CO)$_2$. The result is shown in Table 2.

TABLE 1

| | Catalyst | Ligand 1 (L1) | Ligand 2 (L2) | L1/Rh (mol/mol) | L2/Rh (mol/mol) | N/I | Catalytic activity (mol$_{(BAL)}$/mol$_{(Rh)}$/h) |
|---|---|---|---|---|---|---|---|
| Example 1 | Rh(AcAc)(CO)$_2$ | BPO-P(Pyl)$_2$ | TPPO | 1 | 1 | 8.9 | 262.3 |
| Example 2 | Rh(AcAc)(CO)$_2$ | BPO-P(Pyl)$_2$ | TPPO | 1 | 3 | 8.3 | 256.2 |
| Example 3 | Rh(AcAc)(CO)$_2$ | BPO-P(Pyl)$_2$ | TPPO | 1 | 5 | 8.3 | 270.0 |
| Example 4 | Rh(AcAc)(CO)$_2$ | BPO-P(Pyl)$_2$ | TPPO | 1 | 10 | 8.5 | 264.6 |
| Example 5 | Rh(AcAc)(CO)$_2$ | BPO-P(Pyl)$_2$ | TPPO | 3 | 1 | 13.8 | 227.1 |
| Example 6 | Rh(AcAc)(CO)$_2$ | BPO-P(Pyl)$_2$ | TPPO | 3 | 3 | 13.8 | 181.8 |
| Example 7 | Rh(AcAc)(CO)$_2$ | BPO-P(Pyl)$_2$ | TPPO | 3 | 5 | 14.2 | 176.0 |
| Example 8 | Rh(AcAc)(CO)$_2$ | BPO-P(Pyl)$_2$ | TPPO | 3 | 10 | 14.2 | 182.9 |
| Example 9 | Rh(AcAc)(CO)$_2$ | BPO-P(Pyl)$_2$ | TPPO | 5 | 1 | 16.8 | 140.8 |
| Example 10 | Rh(AcAc)(CO)$_2$ | BPO-P(Pyl)$_2$ | TPPO | 5 | 3 | 16.5 | 148.6 |
| Example 11 | Rh(AcAc)(CO)$_2$ | BPO-P(Pyl)$_2$ | TPPO | 5 | 5 | 16.4 | 143.4 |
| Example 12 | Rh(AcAc)(CO)$_2$ | BPO-P(Pyl)$_2$ | TPPO | 5 | 10 | 16.5 | 140.0 |

TABLE 2

| Catalyst | Ligand (L) | L/Rh Mol/mol | Temp. (°C.) | N/I | Catalytic activity $(mol_{(BAL)}/mol_{(Rh)}/h)$ |
|---|---|---|---|---|---|
| Comparative Example 1 | Rh(AcAc)(CO)$_2$ | TPP | 100 | 85 | 3.9 | 85.4 |
| Comparative Example 2 | Rh(AcAc)(CO)$_2$ | P(Pyl)$_3$ | 50 | 85 | 10.1 | 80.3 |
| Comparative Example 3 | Rh(AcAc)(CO)$_2$ | BPO-P(Pyl)$_2$ | 1 | 85 | 8.7 | 227.3 |
| Comparative Example 4 | Rh(AcAc)(CO)$_2$ | BPO-P(Pyl)$_2$ | 3 | 85 | 14.9 | 179.8 |
| Comparative Example 5 | Rh(AcAc)(CO)$_2$ | BPO-P(Pyl)$_2$ | 5 | 85 | 15.2 | 147.4 |
| Comparative Example 6 | Rh(AcAc)(CO)(TPP) | BPO-P(Pyl)$_2$ | 3 | 85 | 15.0 | 131.4 |

In Comparative Examples 1 and 2, hydroformylation of propene was performed using a monodentate ligand. As described in Table 2, when TPP was used as a ligand (Comparative Example 1), the catalytic activity was 85.4 mol (BAL)/mol(Rh)/h and N/I selectivity was 3.9. When tripyrrolylphosphine (P(Pyl)$_3$) was used as a ligand (Comparative Example 2), the catalytic activity was somewhat lower, but the selectivity of normal-butyraldehyde to iso-butyraldehyde (N/I selectivity 10.1) was somewhat higher than when TPP was used.

As seen from Comparative Examples 3 to 6, when 1,1'-biphenyl-2,2'-diyl-bis(dipyrrolylphosphoramidite) (BPO—P(Pyl)$_2$) as a bidentate ligand was used as a ligand, both catalytic activity and selectivity to normal-butyraldehyde were higher than when either TPP or P(Pyl)$_3$ was used as a ligand. In addition, the use of acetylacetonatodicarbonylrhodium (Rh(AcAc)(CO)$_2$) as a catalyst provided higher catalytic activity than the use of acetylacetonatocarbonyltriphenylphosphinerhodium (Rh(AcAc)(CO)(TPP)).

As described in Table 1, Examples 1 to 12 were performed in the same manner as Comparative Examples 3 to 5 except that TPPO as a monodentate ligand was added to the catalyst composition. The results of Examples 1 to 12 are described below.

As seen from Examples 1 to 4, when 1,1'-biphenyl-2,2'-diyl-bis(dipyrrolylphosphoramidite) (BPO—P(Pyl)$_2$) as a bidentate ligand was used in a molar ratio of 1 based on the catalyst, while adding an increasing molar ratio of TPPO as a monodentate ligand to the catalyst, the catalytic activity was increased by 15 to 20% with the N/I selectivity maintained. As seen from Examples 5 to 12, when the bidentate ligand was used in a molar ratio of at least 3, both the catalyst activity and the N/I selectivity were maintained at each molar ratio of a monodentate ligand TPPO to the catalyst and the stability of the catalyst system was increased using the inexpensive ligand TPPO. That is, even when an excess of TPPO was added to the catalyst system comprising a Rh catalyst and BPO—P(Pyl)$_2$, the catalytic activity was remained constant or even slightly increased and the N/I selectivity was remained constant.

From the above results, it is confirmed that when TPPO as a monodentate ligand is added to the catalyst system comprising acetylacetonatodicarbonylrhodium (Rh(AcAc)(CO)$_2$) as a catalyst and 1,1'-biphenyl-2,2'-diyl-bis(dipyrrolylphosphoramidite) (BPO—P(Pyl)$_2$) as a bidentate ligand, the catalytic activity can be increased by about maximum 20% with the N/I selectivity maintained. Thus, it is possible to perform the hydroformylation reaction in a stable manner using an excess amount of TPPO, which is relatively inexpensive.

The catalyst composition comprising a transition metal catalyst and a combination of a monodentate phosphorous compound and a bidentate phosphorous compound as a ligand according to the embodiment of the present invention can be used in a process of hydroformylation of olefins to produce aldehyde.

A process of hydroformylation of olefins using the catalyst composition comprising a monodentate and a bidentate phosphorous ligand can increase catalytic activity and stability, while maintaining the similar selectivity to normal or iso aldehyde (N/I selectivity) as in the case of using a bidentate ligand alone.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A catalyst composition comprising a bidentate ligand represented by formula 1, a monodentate ligand represented by formula 2, and a transition metal catalyst represented by formula 3:

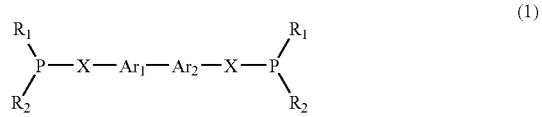

(1)

wherein
each of $R_1$ and $R_2$ is a substituted or unsubstituted C1-20 alkyl group; a substituted or unsubstituted C1-20 alkoxy group; a substituted or unsubstituted C5-20 cycloalkane or cycloalkene; a substituted or unsubstituted C6-36 aryl group; a substituted or unsubstituted C1-20 heteroalkyl group; a substituted or unsubstituted C4-36 heteroaryl group; or a substituted or unsubstituted C4-36 heterocyclic group,
$Ar_1$-$Ar_2$ is a bisaryl compound, and
X is oxygen (O) or sulfur (S),

(2)

wherein
each of $R_3$, $R_4$ and $R_5$ is a substituted or unsubstituted C1-20 alkyl group; a substituted or unsubstituted C1-20 alkoxy group; a substituted or unsubstituted C5-20 cycloalkane or cycloalkene; a substituted or unsubstituted C6-36 aryl group; a substituted or unsubstituted C1-20 heteroalkyl group; a substituted or unsubstituted C4-36 heteroaryl group; or a substituted or unsubstituted C4-36 heterocyclic group, each of $R_3$, $R_4$ and $R_5$ being optionally substituted with nitro (—$NO_2$), fluorine (F), chlorine (Cl), bromine (Br), or a C1-4 alkyl group, and Y is oxygen (O) or sulfur (S),

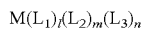  (3)

wherein

M is a transition metal, each of $L_1$, $L_2$ and $L_3$ is hydrogen, CO, acetylacetonato, cyclooctadiene, norbornene, chlorine, or triphenylphosphine, each of l, m and n is a number of 0 to 5, provided that all l, m and n are not zero simultaneously, wherein the concentration of the transition metal is 50 to 500 ppm based on the amount of the catalyst composition, and the concentration of the bidentate ligand is 0.5 to 20 mol and the concentration of the monodentate ligand is 0.1 to 200 mol, respectively, per mol of the transition metal, wherein the transition metal catalyst is acetylacetonatodicarbonylrhodium ($Rh(AcAc)(CO)_2$), the bidentate ligand is 1,1'-biphenyl-2,2'-diyl-bis(dipyrrolylphosphoramidite) (BPO—$P(Pyl)_2$), and the monodentate ligand is triphenylphosphine oxide (TPPO).

2. A process of hydroformylating an olefin compound, comprising reacting the olefin compound with a gas mixture of hydrogen and carbon monoxide with stirring at elevated pressure and temperature in the presence of the catalyst composition of claim 1 to produce an aldehyde.

3. The process of claim 1, wherein the olefin compound is represented by formula 4:

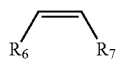  (4)

wherein each of $R_6$ and $R_7$ is hydrogen, a C1-20 alkyl group, fluorine (—F), chlorine (—Cl), bromine (—Br), trifluoromethyl (—$CF_3$), or a C6-20 phenyl group substituted with 0 to 5 substituents selected from the group consisting of nitro (—$NO_2$), fluorine (—F), chlorine (—Cl), bromine (—Br), methyl, ethyl, propyl and butyl.

4. The process of claim 2, wherein the olefin compound is a compound selected from the group consisting of ethene, propene, 1-butene, 1-pentene, 1-hexene, 1-octene, and styrene.

* * * * *